United States Patent
Decoster et al.

(10) Patent No.: US 6,451,298 B1
(45) Date of Patent: *Sep. 17, 2002

(54) COSMETIC COMPOSITIONS COMPRISING AT LEAST ONE SILICONE COPOLYMER AND AT LEAST ONE CATIONIC POLYMER, AND USES THEREOF

(75) Inventors: Sandrine Decoster, Saint Gratien; Véronique Douin, Paris; Virginie Bailly, Clichy, all of (FR)

(73) Assignee: L'Oreal, S.A., Paris (FR)

( * ) Notice: Subject to any disclaimer, the term of this patent is extended or adjusted under 35 U.S.C. 154(b) by 1 day.

This patent is subject to a terminal disclaimer.

(21) Appl. No.: 09/692,357

(22) Filed: Oct. 20, 2000

(30) Foreign Application Priority Data

Oct. 20, 1999 (FR) .............................................. 99 13098

(51) Int. Cl.$^7$ ................................................. A61K 7/06
(52) U.S. Cl. ............................. 424/70.12; 424/70.27; 424/70.28; 524/588
(58) Field of Search ........................... 424/70.12, 70.27, 424/70.28; 524/588

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,632,559 A | 1/1972 | Basel et al. |
| 3,874,870 A | 4/1975 | Green et al. |
| 3,917,817 A | 11/1975 | Vanlerberghe et al. |
| 3,929,990 A | 12/1975 | Green et al. |
| 3,958,581 A * | 5/1976 | Abegg et al. .................. 132/7 |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,131,576 A | 12/1978 | Iovine et al. |
| 4,172,887 A | 10/1979 | Vanlerberghe et al. |
| 4,240,450 A | 12/1980 | Grollier et al. |
| 4,277,581 A | 7/1981 | Vanlerberghe et al. |
| 4,349,532 A | 9/1982 | Vanlerberghe et al. |
| 4,591,610 A | 5/1986 | Grollier |
| 4,608,250 A | 8/1986 | Jacquet et al. |
| 4,761,273 A | 8/1988 | Grollier et al. |
| 4,839,166 A | 6/1989 | Grollier et al. |
| 4,996,059 A | 2/1991 | Grollier et al. |
| 5,139,037 A | 8/1992 | Grollier et al. |
| 5,196,189 A | 3/1993 | Jacquet et al. |
| 6,013,682 A * | 1/2000 | Dalle et al. .................... 516/55 |

FOREIGN PATENT DOCUMENTS

| | | |
|---|---|---|
| EP | 0 080 976 | 6/1983 |
| EP | 0 122 324 | 10/1984 |
| EP | 0 337 354 | 10/1989 |
| EP | 0 787 758 | 8/1997 |
| EP | 0 874 017 | 10/1998 |
| FR | 1 492 597 | 8/1967 |
| FR | 1 583 363 | 10/1969 |
| FR | 2 080 759 | 11/1971 |
| FR | 2 162 025 | 7/1973 |
| FR | 2 190 406 | 1/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |

OTHER PUBLICATIONS

M.R. Porter, "Handbook of Surfactants", Blackie & Son Ltd., Glasgow & London, 1991, pp. 116–178.

English language Derwent Abstract of EP 0 080 976, Jun. 8, 1983.

English language Derwent Abstract of FR 2 080 759, Nov. 19, 1971.

English language Derwent Abstract of FR 2 320 330, Apr. 8, 1977.

English language Derwent Abstract of FR 2 336 434, Aug. 26, 1977.

* cited by examiner

Primary Examiner—Margaret G. Moore
(74) Attorney, Agent, or Firm—Finnegan, Henderson, Farabow, Garrett & Dunner, L.L.P.

(57) ABSTRACT

Cosmetic compositions comprising at least one silicone copolymer with a dynamic viscosity ranging from $1 \times 10^6$ to $100 \times 10^6$ cP and at least one cationic polymer. This combination can give cosmetic properties, such as at least one of smoothness, lightness, and softness, without the phenomenon of regreasing keratin fibers. These compositions can be used for washing and/or conditioning a keratin material, such as the hair or the skin.

91 Claims, No Drawings

COSMETIC COMPOSITIONS COMPRISING AT LEAST ONE SILICONE COPOLYMER AND AT LEAST ONE CATIONIC POLYMER, AND USES THEREOF

The present invention relates to novel cosmetic compositions comprising, in a cosmetically acceptable medium, at least one silicone copolymer defined below, with a dynamic viscosity ranging from $1\times10^6$ to $100\times10^6$ cP and at least one cationic polymer.

It is well known that hair that has been sensitized (i.e. damaged and/or embrittled) to varying degrees under the action of atmospheric agents or mechanical or chemical treatments, such as dyes, bleaches and/or permanent-waving, can be often difficult to disentangle and to style, and may lack softness.

It has already been recommended to use conditioners, in particular cationic polymers or silicones, in compositions for washing or caring for keratin materials such as the hair, in order to facilitate the disentangling of the hair and to give it softness and suppleness. However, the cosmetic advantages mentioned above can be accompanied, on dried hair, by certain cosmetic effects considered undesirable, i.e., lankness of the hairstyle (lack of lightness of the hair) and lack of smoothness (hair not uniform from the root to the tip).

In addition, the use of cationic polymers for this purpose may have various drawbacks. On account of their high affinity for the hair, some of these polymers can become deposited thereon to a large extent during repeated use, and may lead to adverse effects such as an unpleasant, laden feel, stiffening of the hair and interfiber adhesion which may affect styling. These drawbacks may be more accentuated in the case of fine hair, which lacks liveliness and body.

In summary, it is found that the current cosmetic compositions comprising cationic polymers are not always entirely satisfactory.

The inventors have now discovered that the combination of at least one silicone copolymer defined below, with a dynamic viscosity ranging from $1\times10^6$ to $100\times10^6$ cP, with at least one cationic polymer makes it possible to overcome at least one of these drawbacks.

Thus, after considerable research conducted in this matter, the inventors have found that by introducing at least one silicone copolymer with a dynamic viscosity ranging from $1\times10^6$ to $100\times10^6$ cP, into compositions, such as hair compositions containing at least one cationic polymer, it is possible to limit, or even eliminate, at least one of the problems generally associated with the use of such compositions, i.e., for example, the lankness (charged feel following repeated applications) and the lack of smoothness and softness of the hair, while at the same time retaining at least one of the other advantageous cosmetic properties which are associated with conditioner-based compositions.

Moreover, when applied to the skin, for example in the form of a bubble bath or shower gel, the compositions of the invention can provide an improvement in the softness of the skin.

Thus, according to the present invention, cosmetic compositions are now proposed comprising, in a cosmetically acceptable medium, at least one silicone copolymer defined below, wherein said copolymer has a dynamic viscosity ranging from $1\times10^6$ to $100\times10^6$ cP, and at least one cationic polymer.

Another subject of the invention relates to the use of at least one silicone copolymer defined below, with a dynamic viscosity ranging from $1\times10^6$ to $100\times10^6$ cP, in, or for the manufacture of, a cosmetic composition comprising at least one cationic polymer.

The various subjects of the invention will now be described in detail. All the meanings and definitions of the compounds used in the present invention given below are valid for all the subjects of the invention.

The at least one silicone copolymer results from the addition reaction, in the presence of a catalyst, of at least:
(a) one polysiloxane of formula (I):

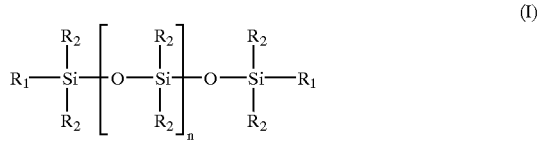

in which:
R$_1$, which may be identical or different, are independently chosen from groups that can react by chain addition reaction such as, for example, a hydrogen atom or aliphatic groups comprising an ethylenic unsaturation, such as vinyl, allyl and hexenyl groups;
R$_2$ in formula (I), which may be identical or different, are independently chosen from hydroxyl, alkyl, alkenyl, cycloalkyl, aryl, and alkylaryl groups, and can optionally further comprise functional groups chosen from ethers, amines, carboxyls, hydroxyls, thiols, esters, sulfonates and sulfates; wherein:
the alkyl groups comprise, for example, 1 to 20 carbon atoms; the alkenyl groups comprise, for example, from 2 to 10 carbon atoms; the cycloalkyl groups comprise, for example, 5 or 6 carbon atoms; the aryl groups comprise, for example, phenyl groups; and the alkylaryl groups comprise, for example, from 7 to 20 carbon atoms;
In one embodiment, R$_2$ is chosen from methyl.
n is an integer wherein the polysiloxane of formula (I) has a kinematic viscosity ranging from 1 to $1\times10^6$ mm$^2$/s, for example, for example n may range from 5 to 5000; and
(b) at least one silicone compound comprising at least one and not more than two groups capable of reacting with the groups R$_1$ of the polysiloxane (a), wherein:
at least one of the compounds of type (a) and (b) comprises an aliphatic group, such as a C$_2$–C$_6$ aliphatic group, comprising an ethylenic unsaturation.

The compounds of type (b) can be another polysiloxane of type (a) in which at least one and not more than two groups R$_1$ of the polysiloxane (b) can react with the groups R$_1$ of the polysiloxane (a).

In one embodiment, the at least one silicone copolymer is obtained by addition reaction, in the presence of a hydrosilylation catalyst (for example a platinum catalyst), of at least:
(a) one α,ω-divinylpolydimethylsiloxane, and
(b) one α,ω-dihydrogenopolydimethylsiloxane.

The silicone copolymer generally has a dynamic viscosity, measured at a temperature of about 25° C. and at a shear rate of 0.01 Hz for a stress of 1500 Pa, ranging from $1\times10^6$ to $100\times10^6$ cP, such as ranging from $5\times10^6$ cP to $30\times10^6$ cP.

All the dynamic viscosity measurements given in the present patent application were taken at a temperature of about 25° C., on a Carri-Medium CSL2-500 machine.

The kinematic viscosity is measured, for example, at 25° C. according to ASTM standard 445 Appendix C.

The at least one silicone copolymer according to the invention is essentially non-crosslinked, i.e., not crosslinked to an extent sufficient to be referred to as a crosslinked copolymer.

Another subject of the invention relates to compositions wherein the at least one silicone copolymer present in the composition is in the form of an aqueous emulsion.

The expression "aqueous emulsion" means an emulsion of oil-in-water type in which the at least one silicone copolymer is dispersed, such as in the form of particles or droplets, in the aqueous phase forming the continuous phase of the emulsion. This emulsion can be stabilized with a common emulsifying system.

This silicone emulsion can have a silicone droplet or particle size ranging from 10 nm to 50 $\mu$m, such as from 0.3 $\mu$m to 20 $\mu$m. The particle size is measured by laser granulometry.

The emulsifying system comprises at least one surfactant commonly used in silicone emulsions. These surfactants may be nonionic, cationic, anionic or amphoteric, or mixtures thereof, such as those described below.

The emulsifying system represents, for example, from 0.5% to 10% by weight relative to the total weight of the emulsion.

The synthesis of these silicone emulsions is described for example in patent application EP-A-874 017, the disclosure of which is incorporated by reference herein.

Such emulsions are sold for example under the name DC2-1997 Cationic Emulsion by the company Dow Corning. This emulsion comprises an $\alpha,\omega$-divinyl-dimethicone/$\alpha,\omega$-dihydrogenodimethicone copolymer with a dynamic viscosity of about $15 \times 10^6$ cP, an emulsifier of cationic type such as cetyltrimethylammonium chloride, a stabilizer such as hydroxyethylcellulose, and water.

The at least one silicone copolymer can be present in a representative amount ranging from 0.05% to 10% by weight relative to the total weight of the composition, such as from 0.1% to 5% by weight relative to the total weight of the composition.

The aqueous emulsion of the at least one silicone copolymer can be present in a representative amount ranging from 0.5% to 15% by weight relative to the total weight of the composition.

The cationic polymers which may be used in accordance with the present invention may be chosen from any of those already known to improve at least one cosmetic property of hair treated with detergent compositions, such as, for example, those described in patent application EP-A-0 337 354 and in French patent applications FR-A-2 270 846, 2 383 660, 2 598 611, 2 470 596 and 2 519 863, the disclosures of which are incorporated herein by reference.

As used herein, "cationic polymer" refers to polymers chosen from polymers comprising at least one cationic groups and polymers comprising at least one group which can be ionized to form cationic groups.

According to the present invention, the at least one cationic polymer may be chosen from polymers which comprise at least one unit comprising at least one group chosen from primary amine groups, secondary amine groups, tertiary amine groups and quaternary amine groups, wherein said at least one group forms part of the polymer skeleton, or is carried by at least one lateral substituent on said polymer skeleton.

According to the present invention, the at least one cationic polymer has a number-average molecular mass generally ranging from about 500 to about $5 \times 10^6$, such as from about $1 \times 10^3$ to about $3 \times 10^6$.

The at least one cationic polymer may be chosen from polymers of quaternary polyammonium type, polymers of polyamino amide type and polymers of polyamine type. Such types of polymers are known in the art.

For example, polymers of the quaternary polyammonium type, polymers of polyamino amide type and polymers of polyamine type which can be used in accordance with the present invention comprise the polymers described in French patents Nos. 2,505,348 and 2,542,997, the disclosures of which are incorporated herein. Non-limiting examples of such polymers include:

(1) homo- and co-polymers derived from at least one monomer chosen from acrylic esters, methacrylic esters and amides, wherein said homo- and co-polymers comprise at least one unit chosen from units of formulae:

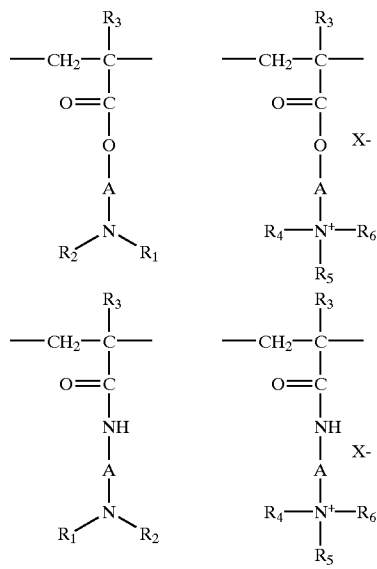

wherein:

$R_3$, which may be identical or different, are each chosen from hydrogen atoms and $CH_3$ groups;

A, which may be identical or different, are each chosen from linear and branched alkyl groups comprising from 1 to 6 carbon atoms, such as 2 or 3 carbon atoms, and hydroxyalkyl groups comprising from 1 to 4 carbon atoms;

$R_4$, $R_5$ and $R_6$, which may be identical or different, are each chosen from alkyl groups comprising from 1 to 18 carbon atoms, such as from 1 to 6 carbon atoms, and benzyl groups;

$R_1$ and $R_2$, which may be identical or different, are each chosen from hydrogen atoms and alkyl groups comprising from 1 to 6 carbon atoms, such as methyl and ethyl;

$X^-$ is an anion chosen from anions derived from at least one inorganic acid and anions derived from at least one organic acid, such as methosulphate anions, and halide atoms, such as chloride atoms and bromide atoms.

Copolymers of family (1) may further comprise at least one unit derived from at least one comonomer chosen from acrylamides, methacrylamides, diacetone acrylamides, acrylamides and methacrylamides, wherein said at least one comonomer is substituted on the nitrogen with at least one group chosen from lower ($C_1$–$C_4$) alkyls, acrylic acids, methacrylic acids, acrylic esters, methacrylic esters, vinyllactams and vinyl esters. Non-limiting examples of vinyllactams include vinylpyrrolidone and vinylcaprolactam.

Non-limiting examples of suitable copolymers are:

copolymers derived from at least one monomer of (i) acrylamide and (ii) dimethylaminoethyl methacrylate quaternized with at least one group chosen from dimethyl sulphate and dimethyl halide, such as the product sold under the name Hercofloc by the company Hercules;

copolymers derived from at least one monomer of (i) acrylamide and (ii) methacryloyloxyethyltrimethylammonium chloride described, for example, in patent application EP-A-080 976, the disclosure of which is incorporated herein by reference, and which is sold under the name Bina Quat P 100 by the company Ciba Geigy;

copolymers derived from at least one monomer of (i) acrylamide and (ii) methacryloyloxyethyltrimethylammonium methosulphate, such as, for example, copolymers sold under the name Reten by the company Hercules;

quaternized and non-quatemized vinylpyrrolidone/dialkylaminoalkyl acrylate copolymers and quatemized and non-quaternized vinylpyrrolidone/dialkylaminoalkyl methacrylate copolymers, such as the products sold under the name "Gafquat" by the company ISP, such as, for example, "Gafquat 734" or "Gafquat 755" and the products known as "Copolymer 845, 958 and 937". These polymers are described in detail in French patents 2 077 143 and 2 393 573, the disclosures of which are incorporated herein by reference;

dimethylaminoethyl methacrylate/vinylcaprolactam/vinylpyrrolidone terpolymers, such as the product sold under the name Gaffix VC 713 by the company ISP;

vinylpyrrolidone/methacrylamidopropyidimethylamine copolymers, such as the product sold under the name Styleze CC 10 by ISP; and quatemized vinylpyrrolidone/dimethylaminopropylmethacrylamide copolymers, such as the product sold under the name "Gafquat HS 100" by the company ISP;

(2) cellulose ether derivatives comprising quaternary ammonium groups, such as those described in French patent 1,492,597, the disclosure of which is incorporated herein by reference, and polymers sold under the names "JR" (JR 400, JR 125 and JR 30M) and "LR" (LR 400, or LR 30M) by the company Union Carbide Corporation. These polymers are also defined in the CTFA dictionary as quaternary ammoniums of hydroxyethylcellulose which has reacted with an epoxide substituted with a trimethylammonium group;

(3) cationic cellulose derivatives such as cellulose copolymers and cellulose derivatives grafted with at least one water-soluble monomer of quatemary ammonium, such as those described in U.S. Pat. No. 4,131,576, the disclosure of which is incorporated herein by reference, such as hydroxyalkylcelluloses (such as, for example, hydroxymethylcelluloses, hydroxyethylcelluloses and hydroxypropylcelluloses, wherein said hydroxyalkylcelluloses are grafted with at least one salt chosen from, for example, methacryloylethyltrimethylammonium salts, methacrylamidopropyltrimethylammonium salts and dimethyidiallylammonium salts). For example, commercial products corresponding to the aforementioned cationic cellulose derivatives include the products sold under the names "Celquat L 200" and "Celquat H 100" by the company National Starch;

(4) cationic polysaccharides, such as those described in U.S. Pat. Nos. 3,589,578 and 4,031,307, the disclosures of which are incorporated herein by reference, such as guar gums comprising at least one cationic trialkylammonium group. For example, guar gums modified with at least one salt, such as a chloride salt, of 2,3-epoxypropyltrimethylammonium may be used in the present invention. Such products are sold in particular under the trade names Jaguar C13 S, Jaguar C 15, Jaguar C 17 and Jaguar C162 by the company Meyhall.

(5) polymers comprising (i) at least one piperazinyl unit and (ii) at least one group chosen from divalent alkylene groups and divalent hydroxyalkylene groups, wherein said at least one group optionally comprises at least one chain chosen from straight chains and branched chains, wherein said at least one chain is optionally interrupted by at least one entity chosen from oxygen atoms, sulphur atoms, nitrogen atoms, aromatic rings and heterocyclic rings, the oxidation products of said polymers and the quaternization products of said polymers. For example, such polymers are described in French patents 2,162,025 and 2,280,361, the disclosures of which are incorporated herein by reference;

(6) water-soluble polyamino amides which may be prepared via at least one polycondensation reaction of at least one acidic compound and at least one polyamine compound, wherein said polyamino amides may be crosslinked with at least one crosslinking agent chosen from epihalohydrins, diepoxides, dianhydrides, unsaturated dianhydrides, bis-unsaturated derivatives, bis-halohydrins, bis-azetidiniums, bis-haloacyldiamines, bis-alkyl halides and oligomers derived from reaction of at least one difunctional compound with at least one compound chosen from bis-halohydrins, bis-azetidiniums, bis-haloacyldiamines, bis-alkyl halides, epihalohydrins, diepoxides and bis-unsaturated derivatives, wherein said crosslinking agent may be used in a proportion generally ranging from 0.025 mol to 0.35 mol per amine group of said polyamino amide, wherein said polyamino amides may optionally be alkylated, and wherein if said polyamino amides comprise at least one tertiary amine group, said polyamino amides may optionally be quaternized. For example, such polymers are described in French patents 2,252,840 and 2,368,508, the disclosures of which are incorporated herein by reference;

(7) polyamino amide derivatives derived from condensation of at least one polyalkylene polyamine with at least one polycarboxylic acid, followed by alkylation with at least one difunctional agent. Non-limiting examples of such polyamino amide derivatives include adipic acid/dialkylaminohydroxyalkyldialkylenetriamine polymers wherein the alkyl group comprises from 1 to 4 carbon atoms, such as methyl groups, ethyl groups and propyl groups. For example, such polymers are described in French patent 1,583,363, the disclosure of which is incorporated herein by reference.

Other non-limiting examples of such derivatives include the adipic acid/dimethylaminohydroxypropyl/diethylenetriamine polymers sold under the name "Cartaretine F, F4 or F8" by the company Sandoz.

(8) polymers derived from reaction of (i) at least one polyalkylene polyamine comprising two primary amine groups and at least one secondary amine group with (ii) at least one dicarboxylic acid chosen from diglycolic acid and saturated aliphatic dicarboxylic acids comprising from 3 to 8 carbon atoms. According to the present invention, the molar ratio of the at least one polyalkylene polyamine to the at least one dicarboxylic acid generally ranges from 0.8:1 to 1.4:1. The polyamino amide resulting from the above reaction may be reacted with epichlorohydrin in a molar ratio of epichlorohydrin to the at least one secondary amine group of the polyamino amide generally ranges from 0.5:1 to 1.8:1. For example, such polymers are described in U.S. Pat. Nos. 3,227,615 and 2,961,347, the disclosures of which are incorporated herein by reference.

Polymers of this type are sold in particular under the name "Hercoseft 57" by the company Hercules Inc. and under the name "PD 170" or "Delsette 101" by the company Hercules in the case of adipic acid/epoxypropyl/diethylenetriamine copolymers.

(9) cyclopolymers of alkyldiallylamine and cyclopolymers of of dialkyldiallylammonium, such as homopolymers and copolymers comprising, as the main constituent of the chain, at least one unit chosen from units of formulae (VI) and (VI'):

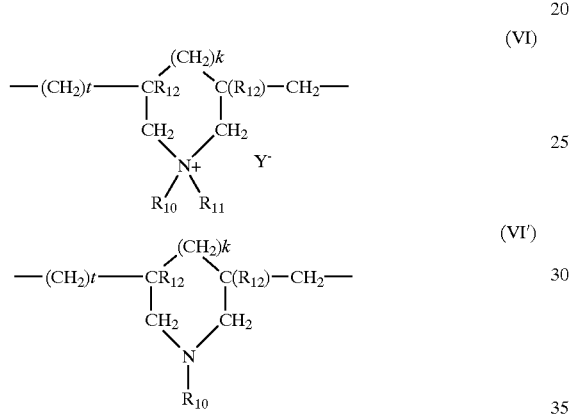

wherein:
k and t, which may be identical or different, are each chosen from 0 and 1, with the proviso that the sum of k+t is equal to 1;
$R_{12}$, which may be identical or different, are each chosen from hydrogen atoms and methyl groups;
$R_{10}$ and $R_{11}$, which may be identical or different, are each chosen from alkyl groups comprising from 1 to 22 carbon atoms, hydroxyalkyl groups wherein alkyl group optionally comprises from 1 to 5 carbon atoms, lower $C_1$–$C_4$ amidoalkyl groups, or $R_{10}$ and $R_{11}$, together with the nitrogen atom to which they are commonly attached, form at least one heterocyclic group, such as piperidyl groups and morpholinyl groups;
$Y^-$ is an anion, such as bromide, chloride, acetate, borate, citrate, tartrate, bisulphate, bisulphite, sulphate and phosphate. For example, such polymers are described in French patent 2,080,759 and in its Certificate of Addition 2,190,406, the disclosures of which are incorporated herein by reference.

In one embodiment, $R_{10}$ and $R_{11}$, which may be identical or different, are each chosen from alkyl groups comprising from 1 to 4 carbon atoms.

Non-limiting examples of the polymers defined above include the dimethyidiallyl-ammonium chloride homopolymer sold under the name "Merquat 100" by the company Calgon (and its homologues of low weight-average molecular mass) and copolymers of diallyldimethylammonium chloride and of acrylamide, sold under the name "Merquat 550".

(10) quatemary diammonium polymers comprising at least two repeating units of formula:

(VII)

wherein:
$R_{13}$, $R_{14}$, $R_{15}$ and $R_{16}$, which may be identical or different, are each chosen from aliphatic groups comprising from 1 to 20 carbon atoms, alicyclic groups comprising from 1 to 20 carbon atoms, arylaliphatic groups comprising from 1 to 20 carbon atoms, lower hydroxyalkylaliphatic groups, or
at least two of said $R_{13}$, $R_{14}$, $R_{15}$ and $R_{16}$, with the nitrogen atoms to which they are attached, form at least one heterocycle optionally comprising an additional heteroatom other than nitrogen, or
$R_{13}$, $R_{14}$, $R_{15}$ and $R_{16}$, which may be identical or different, are each chosen from linear and branched $C_1$–$C_6$ alkyl groups substituted with at least one group chosen from nitrile groups, ester groups, acyl groups, amide groups and groups chosen from groups of formulae —CO—O—$R_{17}$—D and —CO—NH—$R_{17}$—D wherein $R_{17}$ is chosen from alkylene groups and D is chosen from quaternary ammonium groups;
$A_1$ and $B_1$, which may be identical or different, are each chosen from polymethylene groups comprising from 2 to 20 carbon atoms, chosen from linear and branched, saturated and unsaturated polymethylene groups wherein said polymethylene groups may optionally comprise, optionally linked to and optionally intercalated in the main chain, at least one entity chosen from aromatic rings, oxygen atoms, sulphur atoms, sulphoxide groups, sulphone groups, disulphide groups, amino groups, alkylamino groups, hydroxyl groups, quaternary ammonium groups, ureido groups, amide groups and ester groups; and
$X^-$ is an anion chosen from anions derived from inorganic acids and anions derived from organic acids; and
$A_1$, $R_{13}$ and $R_{15}$ may optionally form, together with the two nitrogen atoms to which they are attached, at least one piperazine ring;
with the proviso that if $A_1$ is chosen from linear and branched, saturated and unsaturated alkylene groups and linear and branched, saturated and unsaturated hydroxyalkylene groups, $B_1$ may also be chosen from groups of formula:

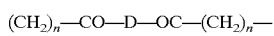

wherein D is chosen from:
a) glycol residues of formula: —O—Z—O—, wherein Z is chosen from linear and branched hydrocarbon groups and groups chosen from groups of formulae:

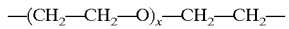

and

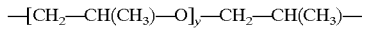

wherein x and y, which may be identical or different, are each chosen from integers ranging from 1 to 4 (in which case x and y represent a defined and unique degree of polymerization) and any number ranging from 1 to 4 (in which case x and y represent an average degree of polymerization);

b) bis-secondary diamine residues such as piperazine derivatives;

c) bis-primary diamine residues chosen from residues of formula: —NH—Y—NH—, wherein Y is chosen from linear and branched hydrocarbon groups and residues of formula —CH$_2$—CH$_2$—S—S—CH$_2$—CH$_2$—; and d) ureylene groups of formula: —NH—CO—NH—.

In one embodiment, X$^-$ is an anion chosen from chloride atoms and bromide atoms.

According to the present invention, the quarternary diammonium polymers have a number-average molecular mass generally ranging from 1000 to 100,000.

For example, polymers of this type are described in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of which are incorporated herein by reference.

Further, according to the present invention, polymers comprising at least two repeating units of formula (a) may be used:

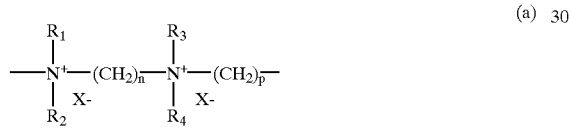

(a)

wherein:

R$_1$, R$_2$, R$_3$ and R$_4$, which may be identical or different, are each chosen from alkyl groups comprising from 1 to 4 carbon atoms approximately and hydroxyalkyl groups comprising from 1 to 4 carbon atoms approximately;

n and p, which may be identical or different, are each chosen from integers ranging from 2 to 20 approximately; and X$^-$ is an anion chosen from anions derived from inorganic acids and anoins derived from organic acids.

In one embodiment, R$_1$, R$_2$, R$_3$ and R$_4$ are chosen from methyl groups, n=3, p=6 and X=Cl. This unit is commonly known as Hexadimethrine chloride according to INCI (CTFA) nomenclature.

(11) polyquaternary ammonium polymers comprising at least one unit of formula (VIII):

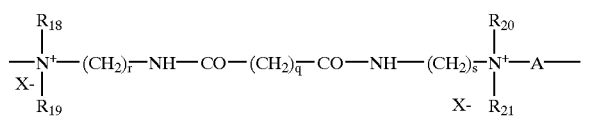

(VIII)

wherein:

R$_{18}$, R$_{19}$, R$_{20}$ and R$_{21}$, which may be identical or different, are each chosen from hydrogen atoms, methyl groups, ethyl groups, propyl groups, β-hydroxyethyl groups, β-hydroxypropyl groups and —CH$_2$CH$_2$(OCH$_2$CH$_2$)$_p$OH groups wherein p is an integer ranging from 0 to 6, with the proviso that R$_{18}$, R$_{19}$, R$_{20}$ and R$_{21}$, are all not simultaneously chosen from hydrogen atoms;

r and s, which may be identical or different, are each chosen from integers ranging from 1 to 6;

q is an integer ranging from 1 to 34;

X$^-$ is an anion, such as a halide,

A is chosen from dihalide groups and groups of formula —CH$_2$—CH$_2$—O—CH$_2$—CH$_2$—.

For example, such compounds are described in patent application EP-A-122,324, the disclosure of which is incorporated by reference.

Non-limiting examples of the polyquarternary ammonium polymers are "Mirapol A 15", "Mirapol AD1", "Mirapol AZ1" and "Mirapol 175" sold by the company Miranol.

(12) quaternary polymers of vinylpyrrolidone and quaternary polymers of vinylimidazole, such as, for example, the products sold under the names Luviquat FC 905, FC 550 and FC 370 by the company BASF.

(13) polyamines, such as Polyquart H sold by Henkel under the reference name "Polyethylene glycol (15) Tallow polyamine" in the CTFA dictionary.

(14) crosslinked (meth)acryloyloxy(C$_1$–C$_4$)alkyltri(C$_1$–C$_4$)alkylammonium salt polymers, such as the polymers derived from homopolymerization of dimethylaminoethyl methacrylate quatemized with methyl chloride and polymers derived from copolymerization, for example, of acrylamide with dimethylaminoethyl methacrylate quaternized with a methyl halide (such as chloride), wherein the homo- or copolymerization is followed by crosslinking with at least one compound comprising olefinic unsaturation, such as methylenebisacrylamide. For example, a crosslinked acrylamide/methacryloyloxyethyltrimethylammonium chloride copolymer (20/80 by weight) in the form of a dispersion comprising about 50% by weight of the said copolymer in mineral oil may be used. This dispersion is sold under the name "Salcare SC 92" by the company Allied Colloids. Further, a crosslinked methacryloyloxyethyltrimethylammonium chloride homopolymer comprising about 50% by weight of the homopolymer in mineral oil or in a liquid ester may be used. These dispersions are sold under the names "Salcare SC 95" and "Salcare SC 96" by the company Allied Colloids.

Other cationic polymers which may be used as the at least one cationic polymer according to the present invention are cationic proteins, cationic protein hydrolysates, polyalkyleneimines (such as polyethyleneimines), polymers comprising at least one vinylpyridine unit, polymers comprising at least one vinylpyridinium unit, condensates of polyamines, condensates of epichlorohydrin, quaternary polyureylenes and chitin derivatives.

For example, quaternary cellulose ether derivatives (such as the products sold under the name "JR 400" by the company Union Carbide Corporation), cationic cyclopolymers (such as the homopolymers or copolymers of dimethyidiallylammonium chloride, sold under the names "Merquat 100", "Merquat 550" and "Merquat S" by the company Calgon), quatemary polymers of vinylpyrrolidone, quaternary polymers of vinylimidazole, crosslinked homopolymers of methacryloyloxy(C$_1$–C$_4$)alkyltri(C$_1$–C$_4$) alkylammonium salts, copolymers of methacryloyloxy (C$_1$–C$_4$)alkyltri(C$_1$–C$_4$)alkylammonium salts, and mixtures of any of the foregoing may be used.

The at least one cationic polymer is present in an amount generally ranging from 0.001% to 20% by weight, such as from 0.01% to 10% by weight and further such as from 0.1% to 3% by weight, relative to the total weight of the final composition.

The compositions of the invention can also comprise at least one surfactant chosen from anionic, amphoteric and nonionic surfactants, which is generally present in an amount ranging from approximately 0.1% to 60% by weight relative to the total weight of the composition, such as from 3% to 40% and further such as from 5% to 30%.

The at least one surfactant chosen from anionic, amphoteric and nonionic surfactants, which are suitable for carrying out the present invention are, for example, the following:

(i) Anionic Surfactant(s)

In the context of the present invention, their nature is not of critical importance.

Representative anionic surfactants include salts (for example alkaline salts, such as sodium salts, ammonium salts, amine salts, amino alcohol salts and magnesium salts) of the following compounds: alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates. The alkyl and acyl radicals of all of these various compounds can for example comprise from 8 to 24 carbon atoms, and the aryl radicals can for example be chosen from phenyl and benzyl groups.

For example, anionic surfactants can be chosen from fatty acid salts such as the salts of oleic, ricinoleic, palmitic and stearic acids, coconut oil acid and hydrogenated coconut oil acid and acyl lactylates in which the acyl radical comprises from 8 to 20 carbon atoms. At least one weakly anionic surfactant can also be used, such as alkyl-D-galactosiduronic acids and their salts, as well as polyoxyalkylenated ($C_6$–$C_{24}$) alkyl ether carboxylic acids, polyoxyalkylenated ($C_6$–$C_{24}$) alkylaryl ether carboxylic acids, polyoxyalkylenated ($C_1$–$C_{24}$) alkylamido ether carboxylic acids and their salts, for example, those comprising from 2 to 50 ethylene oxide groups.

As a further example, the anionic surfactant can be at least one salt chosen from alkyl sulfate salts and alkyl ether sulfate salts.

(ii) Nonionic Surfactant(s)

Useful nonionic surfactants include compounds that are well known per se (see for example in this respect "Handbook of Surfactants" by M. R. Porter, published by Blackie & Son (Glasgow and London), 1991, pp. 116–178), the disclosure of which is incorporated by reference herein, and, in the context of the present invention, their nature is not a critical feature. Thus, nonionic surfactants can include polyethoxylated, polypropoxylated and polyglycerolated fatty acids, alkylphenols, α-diols and alcohols having a fatty aliphatic chain comprising, for example, 8 to 18 carbon atoms, it being possible for the number of ethylene oxide and propylene oxide groups to range for example from 2 to 50 and for the number of glycerol groups to range for example from 2 to 30. Mention may also be made of copolymers of ethylene oxide and of propylene oxide, condensates of ethylene oxide and of propylene oxide with fatty alcohols; polyethoxylated fatty amides for example comprising from 2 to 30 mol of ethylene oxide, polyglycerolated fatty amides comprising on average 1 to 5, such as from 1.5 to 4, glycerol groups; polyethoxylated fatty amines for example comprising from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides and N-acylaminopropylmorpholine oxides. It will be noted that the alkylpolyglycosides are nonionic surfactants that can be suitable in the context of the present invention.

(iii) Amphoteric Surfactant(s)

Representative amphoteric surfactants, whose nature is not a critical feature in the context of the present invention, can be chosen from aliphatic secondary and tertiary amine derivatives in which the aliphatic radical is chosen from linear and branched chain radicals comprising 8 to 22 carbon atoms and comprising at least one water-soluble anionic group (chosen for example from carboxylate, sulfonate, sulfate, phosphate and phosphonate); mention may also be made of ($C_8$–$C_{20}$)alkylbetaines, sulfobetaines, ($C_8$–$C_{20}$) alkylamido($C_1C_6$)alkylbetaines and ($C_8$–$C_{20}$)alkylamido ($C_1$–$C_6$)alkylsulfobetaines.

Representative amine derivatives include the products sold under the name Miranol, as described in U.S. Pat. No. 2,528,378 and 2,781,354, the disclosures of which are incorporated by reference herein, and having the structures:

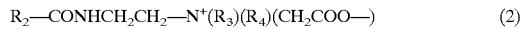

$$R_2\text{—CONHCH}_2\text{CH}_2\text{—N}^+(R_3)(R_4)(CH_2COO\text{—}) \qquad (2)$$

in which:

$R_2$ is chosen from alkyl radicals derived from an acid $R_2$—COOH present in hydrolysed coconut oil, heptyl, nonyl and undecyl radicals, $R_3$ is chosen from β-hydroxyethyl groups, and $R_4$ is chosen from carboxymethyl groups; and

$$R_5\text{—CONHCH}_2\text{CH}_2\text{—N(B)(C)} \qquad (3)$$

in which:

(B) is —CH$_2$CH$_2$OX', with X' chosen from a —CH$_2$CH$_2$—COOH group and a hydrogen atom, (C) is —(CH$_2$)$_z$—Y', with z=1 or 2, and with Y' chosen from —COOH and —CH$_2$—CHOH—SO$_3$H radicals, $R_5$ is chosen from alkyl radicals, such as (a) alkyl radicals of an acid $R_5$—COOH present in oils chosen from coconut oil and hydrolysed linseed oil, (b) alkyl radicals, such as $C_7$, $C_9$, $C_{11}$, and $C_{13}$ alkyl radicals, and (c) $C_{17}$ alkyl radicals and the iso forms, and unsaturated $C_{17}$ radicals.

Such representative compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, and cocoamphodipropionic acid.

By way of example, mention may be made of the cocoamphodiacetate sold under the trade name Miranol C2M Concentrate by the company Rhône-Poulenc.

In the compositions in accordance with the invention, at least two surfactants of different types can be used. Representative compositions include compositions comprising (a) more than one anionic surfactant, (b) at least one anionic surfactant and at least one amphoteric surfactant, and (c) at least one anionic surfactant and at least one nonionic surfactant. In one embodiment, the composition can comprise at least one anionic surfactant and at least one amphoteric surfactant.

The at least one anionic surfactant used for example, can be chosen from ($C_{12}$–$C_{14}$)alkyl sulfates of sodium, of triethanolamine and of ammonium; ($C_{12}$–$C_{14}$)alkyl ether sulfates of sodium, of triethanolamine and of ammonium, oxyethylenated with 2.2 mol of ethylene oxide; sodium cocoyl isethionate; and sodium ($C_{14}$–$C_{16}$)-α-olefin sulfonate, and used in combination with an amphoteric surfactant chosen from either: amphoteric surfactants such as the amine derivatives known as disodium cocoamphodipropionate and sodium cocoamphopropionate, sold for example by the company Rhône-Poulenc under the trade name "Miranol C2M Conc®" as an aqueous solution comprising 38% active material, and under the name Miranol C32; or amphoteric surfactants of zwitterionic type, such as alkylbetaines, for example the cocobetaine sold under the name "Dehyton AB 30" as an aqueous solution comprising 32% AM by the company Henkel.

In one embodiment of the invention, the compositions can also comprise at least one cationic surfactant.

Representative at least one cationic surfactants can be chosen from salts of optionally polyoxyalkylenated primary, secondary and tertiary fatty amines; quaternary ammonium salts; imidazoline derivatives; and amine oxides of cationic nature.

The at least one cationic surfactant may, for example, be chosen from:

A) quaternary ammonium salts of formula (IV) below:

(IV)

in which:
the radicals $R_1$ $R_2$, $R_3$, and $R_4$, which may be identical or different, are independently chosen from linear and branched aliphatic radicals comprising from 1 to 30 carbon atoms, and aromatic radicals, such as $C_6$–$C_{20}$ aromatic radicals (for example, aryl and alkylaryl), wherein the aliphatic radicals can comprise hetero atoms such as, oxygen, nitrogen, sulfur and halogens, and wherein the aliphatic radicals are chosen, for example, from alkyl, alkoxy, polyoxy ($C_2$–$C_6$)alkylene, alkylamide, ($C_{12}$–$C_{22}$)alkylamido ($C_2$–$C_6$)alkyl, ($C_{12}$–$C_{22}$)alkylacetate and hydroxyalkyl radicals, comprising from 1 to 30 carbon atoms;

$X^-$ is an anion chosen from halides, phosphates, anions derived from organic acids, ($C_2$–$C_6$)alkyl sulfates, alkyl sulfonates, and alkylaryl sulfonates.

The compounds of formula (IV) can be chosen from, for example, (a) compounds comprising at least two fatty aliphatic radicals comprising from 8 to 30 carbon atoms, (b) compounds comprising at least one fatty aliphatic radical comprising from 17 to 30 carbon atoms, and (c) compounds comprising at least one aromatic radical.

B) Quaternary ammonium salts of imidazolinium, such as, for example, the salts of formula (V) below:

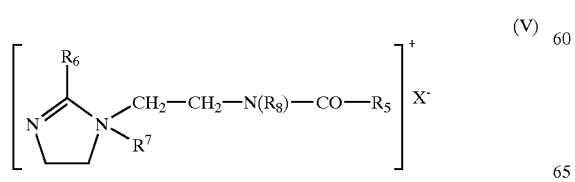

(V)

in which:
$R_5$ is chosen from alkenyl and alkyl radicals comprising from 8 to 30 carbon atoms, for example radicals derived from tallow fatty acid, $R_6$ is chosen from a hydrogen atom, $C_1$–$C_4$ alkyl radicals, and alkenyl and alkyl radicals comprising from 8 to 30 carbon atoms, $R_7$ is chosen from $C_1$–$C_4$ alkyl radicals, $R_8$ is chosen from a hydrogen atom and $C_1$–$C_4$ alkyl radicals, $X^-$ is an anion chosen from halides, phosphates, acetates, lactates, alkyl sulfates, alkyl sulfonates, and alkylaryl sulfonates.

For example, $R_5$ and $R_6$, which may be identical or different, are independently chosen from alkenyl and alkyl radicals comprising from 12 to 21 carbon atoms, for example, radicals derived from tallow fatty acid, $R_7$ is methyl, and $R_8$ is hydrogen.

Such products are, for example, (1) Quaternium-27 (International Cosmetic Ingredient Dictionary and Handbook, hereafter "CTFA", 1997), i.e., "Rewoquat" W75, W75PG, and W90, and (2) Quatemium-83 (CTFA 1997), i.e., "Rewoquat" W75HPG, which are sold by the company Witco.

C) Diquaternary ammonium salts of formula (VI):

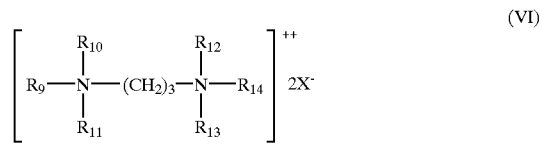

(VI)

in which:
$R_9$ is chosen from aliphatic radicals comprising from 16 to 30 carbon atoms, $R_{10}$, $R_{11}$, $R_{12}$, $R_{13}$ and $R_{14}$, which may be identical or different, are independently chosen from a hydrogen atom and alkyl radicals comprising from 1 to 4 carbon atoms, and $X^-$ is an anion chosen from halides, acetates, phosphates, nitrates and methyl sulfates.

For example, such diquaternary ammonium salts can comprise propane tallow diammonium dichloride.

D) Quaternary ammonium salts comprising at least one ester function. The quaternary ammonium salts comprising at least one ester function that can be used according to the invention are, for example, those of formula (VII) below:

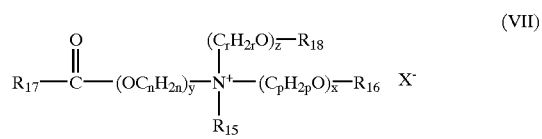

(VII)

in which:
R$_{15}$ is chosen from C$_1$–C$_6$ alkyl radicals and C$_1$–C$_6$ hydroxyalkyl and C$_1$–C$_6$ dihydroxyalkyl radicals;
R$_{16}$ is chosen from:
acyl groups of the following formula:

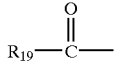

wherein R$_{19}$ is defined below,
linear and branched, saturated and unsaturated, C$_1$–C$_{22}$ hydrocarbon-based radicals, and
a hydrogen atom;
R$_{18}$ is chosen from:
acyl groups of the following formula:

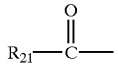

wherein R$_{21}$ is defined below,
linear and branched, saturated and unsaturated, C$_1$–C$_6$ hydrocarbon-based radicals, and
a hydrogen atom;
R$_{17}$, R$_{19}$ and R$_{21}$, which may be identical or different, are independently chosen from linear and branched, saturated and unsaturated, C$_7$–C$_{21}$ hydrocarbon-based radicals;
n, p and r, which may be identical or different, are independently integers ranging from 2 to 6;
y is an integer ranging from 1 to 10;
x and z, which may be identical or different, are independently integers ranging from 0 to 10;
X$^-$ is chosen from simple and complex, organic and inorganic anions;
provided that the sum x+y+z is from 1 to 15, and that when x is 0, then R$_{16}$ is chosen from linear and branched, saturated and unsaturated, C$_1$–C$_{22}$ hydrocarbon-based radicals, and that when z is 0, then R$_{18}$ is chosen from linear and branched, saturated and unsaturated, C$_1$–C$_6$ hydrocarbon-based radicals.

In one embodiment, the R$_{15}$ alkyl radicals may be linear and branched and further, for example, linear.

For example, R$_{15}$ may be chosen from methyl, ethyl, hydroxyethyl and dihydroxypropyl radicals and further for example from methyl and ethyl radicals.

The sum x+y+z may for example range from 1 to 10.

When R$_{16}$ is chosen from linear and branched, saturated and unsaturated, C$_1$–C$_{22}$ hydrocarbon-based radicals, R$_{16}$ may be long and comprise from 12 to 22 carbon atoms, or short and comprise from 1 to 3 carbon atoms.

When R$_{18}$ is chosen from linear and branched, saturated and unsaturated, C$_1$–C$_6$ hydrocarbon-based radicals, R$_{18}$ may for example comprise from 1 to 3 carbon atoms.

R$_{17}$, R$_{19}$ and R$_{21}$, which may be identical or different, can, for example, be independently chosen from linear and branched, saturated and unsaturated C$_{11}$–C$_{21}$ hydrocarbon-based radicals, and for example from linear and branched, saturated and unsaturated, C$_{11}$–C$_{21}$ alkyl and alkenyl radicals. x and z, which may be identical or different, can for example independently be chosen from 0 or 1.

y for example may be equal to 1.

n, p and r, which may be identical or different, can for example be independently chosen from 2 and 3 and in one embodiment equal to 2.

The anion for example can be chosen from halides (chloride, bromide, and iodide) and alkyl sulfates, such as methyl sulfate. However, methanesulfonate, phosphate, nitrate, tosylate, anions derived from organic acids, such as acetate and lactate, and any other anions compatible with the ammonium comprising an ester function, may be used.

As a further example, the anion X$^-$ can be chosen from chloride and methyl sulfate.

Further examples of ammonium salts of formula (VII) are those in which:
R$_{15}$ is chosen from methyl and ethyl radicals,
x and y are equal to 1;
z is equal to 0 or 1;
n, p and r are equal to 2;
R$_{16}$ is chosen from:
acyl radicals

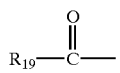

wherein R$_{19}$ is defined below,
methyl, ethyl and C$_{14}$–C$_{22}$ hydrocarbon-based radicals, and
a hydrogen atom;
R$_{18}$ is chosen from:
acyl radicals

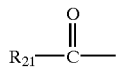

wherein R$_{21}$ is defined below,
a hydrogen atom;
R$_{17}$, R$_{19}$ and R$_{21}$, which may be identical or different, are independently chosen from linear and branched, saturated and unsaturated, C$_{13}$–C$_{17}$ hydrocarbon-based radicals, such as from linear and branched, saturated and unsaturated C$_{13}$–C$_{17}$ alkyl and alkenyl radicals.

The hydrocarbon-based radicals can for example be linear.

Representative compounds of formula (VII) are chosen from diacyloxyethyldimethylammonium, diacyloxyethylhydroxyethylmethylammonium, monoacyloxyethyidihydroxyethylmethylammonium, triacyloxyethylmethylammonium and monoacyloxyethylhydroxyethyidimethylammonium salts (for example chloride and methyl sulfate). The acyl radicals can for example comprise from 14 to 18 carbon atoms and can for example be obtained from plant oils, such as palm oil and sunflower oil. When the compound comprises several acyl radicals, these radicals, which may be independently chosen, may independently be identical or different.

These products are obtained, for example, by direct esterification of compounds chosen from triethanolamine, triisopropanolamine, alkyldiethanolamines and alkyldiisopropanolamines, which are optionally oxyalkylenated, with fatty acids or with fatty acid mixtures of plant or animal origin, and by transesterification of the methyl esters thereof. This esterification is followed by a quatemization using an alkylating agent such as alkyl halides (such ad methyl and ethyl halides), dialkyl sulfates (for example dimethyl and diethyl sulfates), methyl methanesulfonate, methyl paratoluenesulfonate, glycol chlorohydrin and glycerol chlorohydrin.

Such compounds are sold, for example, under the names Dehyquart by the company Henkel, Stepanquat by the company Stepan, Noxamium by the company Ceca and Rewoquat WE 18 by the company Rewo-Witco.

It is also possible to use the ammonium salts comprising at least one ester function, described in patents U.S. Pat. Nos. 4,874,554 and U.S. Pat. No. 4,137,180, the disclosures of which are incorporated by reference herein.

Representative quaternary ammonium salts of formula (IV) include tetraalkylammonium chlorides such as, for example, dialkyldimethylammonium chlorides and alkyltrimethylammonium chlorides, in which the alkyl radical comprises from 12 to 22 carbon atoms, for example behenyltrimethylammonium chloride, distearyldimethylammonium chloride, cetyltrimethylammonium chloride, and benzyldimethylstearylammonium chloride, and, stearamidopropyldimethyl(myristyl acetate)ammonium chloride sold under the name "Cepharyl 70" by the company Van Dyk.

According to the invention, the at least one cationic surfactant can for example be present in an amount ranging from 0.1% to 20% by weight relative to the total weight of the final composition, such as from 0.1% to 10%, from 0.5% to 7%, and further such as from 1% to 5% by weight relative to the total weight of the final composition.

The composition of the invention can also comprise at least one additive chosen from thickeners, fragrances, nacreous agents, preserving agents, silicone sunscreens, non-silicone sunscreens, vitamins, provitamins, amphoteric, anionic and nonionic polymers, proteins, protein hydrolysates, 18-methyleicosanoic acid, hydroxy acids, panthenol, volatile and non-volatile, cyclic and linear and crosslinked, modified and non-modified silicones, ceramides, pseudoceramides, plant, animal, mineral and synthetic oils, and any other additive conventionally used in cosmetics which does not substantially adversely affect the properties of the compositions according to the invention.

Generally, these additives are present in the composition according to the invention in amounts, for example, ranging from 0 to 20% by weight relative to the total weight of the composition. The precise amount of each additive is readily determined by those skilled in the art depending on its nature and its function.

The compositions in accordance with the invention can also be used for washing or treating at least one keratin material chosen from hair, skin, eyelashes, eyebrows, nails, lips, scalp, and hair.

The compositions according to the invention can also be a detergent composition chosen from shampoos, shower gels, bubble baths and make-up-removing products. In this embodiment of the invention, the compositions comprise a washing base, which is generally aqueous.

At least one surfactant forms the washing base and can be chosen from anionic, amphoteric, nonionic and cationic surfactants, such as those defined above.

The quantity and quality of the washing base are sufficient to give the final composition at least one of the following qualities, satisfactory foaming power and satisfactory detergent power.

According to the invention, the washing base can be present for example in an amount ranging from 4% to 50% by weight, such as from 6% to 35% by weight and even further such as from 8% to 25% by weight, relative to the total weight of the final composition.

Another subject of the invention is also a process for treating at least one keratin material, such as the skin and the hair, comprising applying a cosmetic composition as defined above to the at least one keratin material and optionally rinsing it out with water.

Thus, this process according to the invention allows maintenance of the hairstyle and treatment of, care of, washing of or removal of make-up from the skin, the hair or any other keratin material.

The compositions of the invention can for example be in forms chosen from rinse-out conditioners and leave-in conditioners; permanent-waving, straightening, dyeing and bleaching compositions; rinse-out compositions to be applied before a procedure chosen from dyeing, bleaching, permanent-waving and straightening the hair; rinse-out compositions to be applied after a procedure chosen from dyeing, bleaching, permanent-waving and straightening the hair; and rinse-out compositions to be applied between the two steps of a procedure chosen from permanent-waving and straightening the hair.

The compositions according to the invention can also be in a form chosen from aqueous and aqueous-alcoholic lotions for a care chosen from skin care and hair care.

The cosmetic compositions according to the invention can be in a form chosen from gels, milks, creams, emulsions, thickened lotions and mousses and can be used for treating at least one keratin material chosen from skin, nails, eyelashes, lips, and hair.

The compositions can be packaged in various forms chosen from vaporizers, pump-dispenser bottles and aerosol containers in order to ensure application of the composition in vaporized form or in the form of a mousse. Such packaging forms are indicated, for example, when it is desired to obtain a spray, a lacquer or a mousse for treating the hair.

In all of the text hereinabove and hereinbelow, the percentages expressed are on a weight basis.

The invention will now be illustrated more fully with the aid of the examples which follow, which should not be considered as limiting it to the embodiments described. In the examples, AM means active material.

EXAMPLE 1

A conditioner in accordance with the invention, having the following composition, was prepared:

| | |
|---|---|
| Mixture of glyceryl mono-, di- and tristearate | 1 g |
| Glycerol | 0.5 g |
| Polyquaternium-11 as an aqueous solution containing 20% active material (AM) (Gafquat 755 from ISP) | 0.5 gAM |
| Polyquaternium-30 as an aqueous-alcoholic solution containing 22% AM (Mexomere PX from Chimex) | 0.55 gAM |
| Behenyltrimethylammonium chloride (Genamin KDMP from Clariant) | 1.45 gAM |
| Cationic emulsion containing 67% AM of a copolymer of polydimethylsiloxane containing α, ω-vinyl groups/polydimethylsiloxane containing α, ω-hydrogeno groups (DC-1997 from Dow Corning) | 0.8 gAM |
| Mixture of cetyl alcohol and of stearyl alcohol (50/50 by weight) | 4 g |
| Fragrance, preserving agents | qs |
| Water qs | 100 g |

This composition is applied to washed and dried hair. It is left to stand on the hair for 2 minutes and is then rinsed off with water.

Hair treated with this conditioner is soft, smooth and disentangles easily.

EXAMPLE 2

A conditioner in accordance with the invention, having the following composition, was prepared:

| | |
|---|---|
| Cationic emulsion containing 67% AM of copolymer of polydimethylsiloxane containing α, ω-vinyl groups/polydimethylsiloxane containing α,, ω-hydrogeno groups (DC-1997 from Dow Corning) | 5 gMA |
| SMDI/polyethylene glycol/alkyl (methyl/C18) endings copolymer at a concentration of 15% in a maltodextrin/water matrix (Aculyn 46 from Rohm & Haas) | 0.45 gAM |
| crosslinked ethyltrimethylammonium methacrylate chloride homopolymer as a reverse emulsion at a concentration of 50% in mineral oil (Salcare SC 95 from Ciba Geigy) | 0.55 gAM |
| Mixture of cetyl alcohol and of stearyl alcohol (50/50 by weight) | 6 g |
| Fragrance, preserving agents | qs |
| Water qs | 100 g |

EXAMPLE 3

A shampoo in accordance with the invention, having the composition below, was prepared:

| | |
|---|---|
| Cationic emulsion containing 67% AM of copolymer of polydimethylsiloxane containing α, ω-vinyl groups/polydimethylsiloxane containing α, ω-hydrogeno groups (DC-1997 from Dow Corning) | 1.95 gMA |
| Sodium lauryl ether sulphate oxyethylenated with 2.2 mol of ethylene oxide, as an aqueous solution containing 70% AM | 15.3 gAM |
| Imidazoline-based surfactant as an aqueous solution containing 38% active material (Miranol C2M conc. from Rhodia Chimie) | 3.05 gAM |
| Guar gum modified with 2,3-epoxypropyl-trimethylammonium chloride (Jaguar C13S from Rhodia Chimie) | 0.2 g |
| Mixture of stearyl alcohol (10%) and of distearyl ether (90%) | 1.5 g |
| Mixture of linear alcohols (C18/C20/C22) (Nafol 1822 C from Condea) | 1.5 g |
| Lauryl alcohol oxyethylenated with 2.5 mol of ethylene oxide | 0.75 g |
| Coconut acid monoisopropanolamide | 0.4 g |
| Crosslinked polyacrylic acid | 0.2 g |
| Vitamin B3, vitamin B6 | qs |
| Fruit extract | qs |
| Preserving agents, fragrance | qs |
| Citric acid monohydrate, qs | pH 7.5 |
| Demineralized water qs | 100 g |

What is claimed is:

1. A cosmetic composition comprising, in a cosmetically acceptable medium, (1) at least one silicone copolymer with a dynamic viscosity ranging from $1 \times 10^6$ to $100 \times 10^6$ cP, resulting from the addition reaction, in the presence of a catalyst, of at least:

(a) one polysiloxane of formula (I):

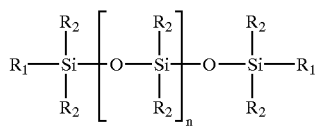

(I)

in which:

R$_1$, which may be identical or different, are independently chosen from groups that can react by chain addition reaction, R$_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups R$_1$ of the polysiloxane (a), wherein:

at least one of the compounds of type (a) and (b) comprises an aliphatic group comprising an ethylenic unsaturation, and (2) at least one cationic polymer.

2. A composition according to claim 1, wherein R$_1$ is chosen from a hydrogen atom and aliphatic groups comprising an ethylenic unsaturation.

3. A composition according to claim 2, wherein the aliphatic groups comprising an ethylenic unsaturation are chosen from vinyl, allyl and hexenyl groups.

4. A composition according to claim 1, wherein the groups R$_2$ are chosen from hydroxyl groups; alkyl groups comprising from 1 to 20 carbon atoms; cycloalkyl groups comprising from 5 to 6 carbon atoms; phenyl groups; alkylaryl groups comprising from 7 to 20 carbon atoms; and can optionally further comprise functional groups chosen from ethers, amines, carboxyls, hydroxyls, thiols, esters, sulfonates and sulfates.

5. A composition according to claim 1, wherein said alkenyl groups are chosen from alkenyl groups comprising from 2 to 10 carbon atoms.

6. A composition according to claim 1, wherein R$_2$ is a methyl group.

7. A composition according to claim 1, wherein n is an integer ranging from 5 to 5,000.

8. A composition according to claim 1, wherein the compound of type (b) is another polysiloxane of type (a) in which at least one and not more than two groups R$_1$ of the polysiloxane (b) can react with the groups R$_1$ of the polysiloxane (a).

9. A composition according to claim 1, wherein, in the presence of a hydrosilylation catalyst, the at least one silicone copolymer is obtained by addition reaction of at least:

(a) one α,ω-divinylpolydimethylsiloxane, and (b) one α,ω-dihydrogenopolydimethylsiloxane.

10. A composition according to claim 9, wherein the hydrosilylation catalyst is a platinum catalyst.

11. A composition according to claim 1, wherein said at least one silicone copolymer is in the form of an aqueous emulsion.

12. A composition according to claim 1, wherein the at least one silicone copolymer is essentially non-crosslinked.

13. A composition according to claim 1, wherein the at least one silicone copolymer is present in an amount ranging from 0.05% to 10% by weight relative to the total weight of the composition.

14. A composition according to claim 13, wherein the at least one silicone copolymer is present in an amount ranging from 0.1% to 5% by weight relative to the total weight of the composition.

15. A composition according to claim 11, wherein said aqueous emulsion of the at least one silicone copolymer has a silicone droplet or particle size ranging from 10 nm to 50 μm.

16. A composition according to claim 15, wherein said emulsion of the at least one silicone copolymer has a silicone droplet or particle size ranging from 0.3 µm to 20 µm.

17. A composition according to claim 1 further comprising at least one cationic surfactant chosen from:

A) quaternary ammonium salts of formula (IV) below:

in which:
the radicals $R_1$, $R_2$, $R_3$, and $R_4$, which may be identical or different, are independently chosen from linear and branched aliphatic radicals comprising from 1 to 30 carbon atoms, and aromatic radicals, wherein the aliphatic radicals optionally comprise hetero atoms, and $X^-$ is an anion chosen from the group of halides, phosphates, anions derived from organic acids, ($C_2$–$C_6$)alkyl sulfates, alkyl sulfonates, and alkylaryl sulfonates;

B) quaternary ammonium salts of imidazolinium of formula (V) below:

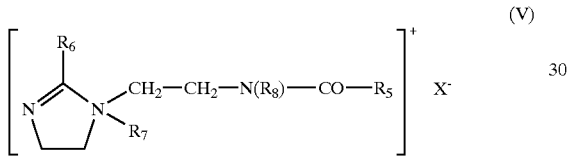

in which:
$R_5$ is chosen from alkenyl and alkyl radicals comprising from 8 to 30 carbon atoms, $R_6$ is chosen from a hydrogen atom, $C_1$–$C_4$ alkyl radicals, and alkenyl and alkyl radicals comprising from 8 to 30 carbon atoms, $R_7$ is chosen from $C_1$–$C_4$ alkyl radicals, $R_8$ is chosen from a hydrogen atom and $C_1$–$C_4$ alkyl radicals, and $X^-$ is an anion chosen from halides, phosphates, acetates, lactates, alkyl sulfates, alkyl sulfonates, and alkylaryl sulfonates;

C) diquaternary ammonium salts of formula (VI):

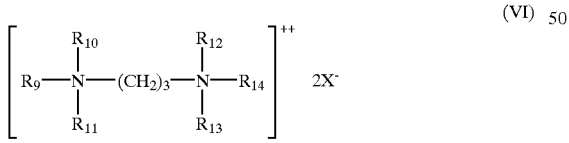

in which:
$R_9$ is chosen from aliphatic radicals comprising from 16 to 30 carbon atoms, $R_{10}$, $R_{11}$, $R_{12}$, $R_{13}$ and $R_{14}$, which may be identical or different, are independently chosen from a hydrogen atom and alkyl radicals comprising from 1 to 4 carbon atoms, and $X^-$ is an anion chosen from halides, acetates, phosphates, nitrates and methyl sulfates;

D) quaternary ammonium salts of formula (VII) below comprising at least one ester function:

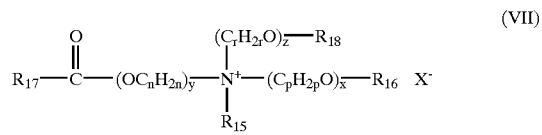

in which:
$R_{15}$ is chosen from $C_1$–$C_6$ alkyl radicals and $C_1$–$C_6$ hydroxyalkyl and $C_1$–$C_6$ dihydroxyalkyl radicals;

$R_{16}$, is chosen from:
acyl groups of the following formula:

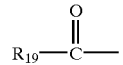

wherein $R_{19}$ is defined below,
linear and branched, saturated and unsaturated, $C_1$–$C_{22}$ hydrocarbon-based radicals, and
a hydrogen atom;

$R_{18}$ is chosen from:
acyl groups of the following formula:

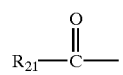

wherein $R_{21}$ is defined below,
linear and branched, saturated and unsaturated, $C_1$–$C_6$ hydrocarbon-based radicals, and
a hydrogen atom;

$R_{17}$, $R_{19}$ and $R_{21}$, which may be identical or different, are independently chosen from linear and branched, saturated and unsaturated, $C_7$–$C_{21}$ hydrocarbon-based radicals;

n, p and r, which may be identical or different, are independently integers ranging from 2 to 6;

y is an integer ranging from 1 to 10;

x and z, which may be identical or different, are independently integers ranging from 0 to 10; and $X^-$ is chosen from simple and complex, organic and inorganic anions; and provided that the sum x+y+z is from 1 to 15, and that when x is 0, then $R_{16}$ is chosen from linear and branched, saturated and unsaturated, $C_1$–$C_{22}$ hydrocarbon-based radicals, and that when z is 0, then $R_{18}$ is chosen from linear and branched, saturated and unsaturated, $C_1$–$C_6$ hydrocarbon-based radicals.

18. A composition according to claim 17, wherein said at least one cationic surfactant is chosen from:

A) quaternary ammonium salts of formula (IV) below:

wherein:
$X^-$ is an anion chosen from halides, ($C_2$–$C_6$)alkyl sulfates, phosphates, alkyl and alkylaryl sulfonates, and anions derived from organic acids, and i) the radicals $R_1$, $R_2$, and $R_3$, which may be identical or different, are independently chosen from linear and branched aliphatic radicals comprising from 1 to 4 carbon atoms, optionally comprising hetero atoms, and aromatic radicals, and R$_4$ is chosen from linear and branched alkyl radicals comprising from 16 to 30 carbon atoms;

ii) the radicals R$_1$ and R$_2$, which may be identical or different, are independently chosen from linear and branched aliphatic radicals comprising from 1 to 4 carbon atoms, optionally comprising hetero atoms, and aromatic radicals, and R$_3$ and R$_4$, which may be identical or different, are independently chosen from linear and branched alkyl radicals comprising from 12 to 30 carbon atoms, wherein said radicals further comprise at least one function chosen from ester and amide functions.

19. A composition according to claim 17, wherein in said quaternary ammonium salts of formula (VII):

R$_{15}$ is chosen from methyl and ethyl radicals, x and y are equal to 1;

z is equal to 0 or 1;

n, p and r are equal to 2;

R$_{16}$ is chosen from:
acyl radicals

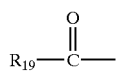

wherein R$_{19}$ is defined below,
methyl, ethyl and C$_{14}$–C$_{22}$ hydrocarbon-based radicals, and
a hydrogen atom;

R$_{18}$ is chosen from:
acyl radicals

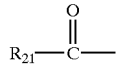

wherein R$_{21}$ is defined below,
a hydrogen atom; and

R$_{17}$, R$_{19}$ and R$_{21}$, which may be identical or different, are independently chosen from linear and branched, saturated and unsaturated, C$_{13}$–C$_{17}$ hydrocarbon-based radicals.

20. A composition according to claim 19, wherein R$_{17}$, R$_{19}$ and R$_{21}$ are chosen from linear and branched, saturated and unsaturated C$_{13}$–C$_{17}$ aliphatic radicals.

21. A composition according to claim 19, wherein the hydrocarbon-based radicals are chosen from linear hydrocarbon-based radicals.

22. A composition according to claim 17, wherein the compounds of formula (VII) are chosen from diacyloxyethyidimethylammonium, diacyloxyethylhydroxyethylmethylammonium, monoacyloxyethyidihydroxyethylmethylammonium, triacyloxyethylmethylammonium and monoacyloxyethylhydroxyethyldimethylammonium salts.

23. A composition according to claim 22, wherein said monoacyloxyethylhydroxyethyldimethylammonium salts are chosen from monoacyloxyethylhydroxyethyldimethylammonium chloride salts and monoacyloxyethylhydroxyethyldimethylammonium methyl sulfate salts.

24. A composition according to claim 19, wherein when R$_{16}$ and R$_{18}$ are chosen from acyl radicals, said acyl radicals are obtained from plant oils chosen from palm oil and sunflower oil.

25. A composition according to claim 17, wherein X$^-$ of said quaternary ammonium salts of formula (IV) is an anion chosen from chloride, bromide, iodide, methyl sulfate, acetate, and lactate.

26. A composition according to claim 17, wherein said aromatic radicals of said quaternary ammonium salts of formula (IV) are chosen from aryl and alkylaryl.

27. A composition according to claim 17, wherein said hetero atoms of said quaternary ammonium salts of formula (IV) are chosen from oxygen, nitrogen, sulfur and halogens.

28. A composition according to claim 18, wherein said aliphatic radicals of formula (IV)(ii) are chosen from alkyl, alkoxy, alkylamide, polyoxy(C$_2$–C$_6$)alkylene, and hydroxyalkyl radicals comprising from 1 to 4 carbon atoms.

29. A composition according to claim 18, wherein said R$_3$ and R$_4$ of formula (IV)(ii) are chosen from (C$_{12}$–C$_{22}$) alkylamido(C$_2$–C$_6$)alkyl and (C$_{12}$–C$_{22}$)alkylacetate radicals.

30. A composition according to claim 17, wherein said R$_5$ of formula (V) is chosen from radicals derived from tallow fatty acid.

31. A composition according to claim 17, wherein in said quaternary ammonium salts of imidazolinium of formula (V):

R$_5$ and R$_6$, which may be identical or different, are independently chosen from alkenyl and alkyl radicals comprising from 12 to 21 carbon atoms, R$_7$ is methyl, and R$_8$ is hydrogen.

32. A composition according to claim 31, wherein said R$_5$ and R$_6$, which may be identical or different, are independently chosen from radicals derived from tallow fatty acid.

33. A composition according to claim 17, wherein said diquaternary ammonium salts comprise propane tallow diammonium dichloride.

34. A composition according to claim 17, wherein said R$_{15}$ alkyl radicals of said quaternary ammonium salts of formula (VII) are chosen from linear and branched C$_1$–C$_6$ alkyl radicals.

35. A composition according to claim 34, wherein said R$_{15}$ radicals are linear radicals.

36. A composition according to claim 35, wherein said R$_{15}$ radicals are chosen from methyl, ethyl, hydroxyethyl and dihydroxypropyl.

37. A composition according to claim 36, wherein said R$_{15}$ radicals are chosen from methyl and ethyl.

38. A composition according to claim 17, wherein said sum of x+y+z of said quaternary ammonium salts of formula (VII) ranges from 1–10.

39. A composition according to claim 17, wherein said quaternary ammonium salts of formula (IV) are chosen from (a) compounds comprising at least two fatty aliphatic radicals comprising from 8 to 30 carbon atoms, (b) compounds comprising at least one fatty aliphatic radical comprising from 17 to 30 carbon atoms, and (c) compounds comprising at least one aromatic radical.

40. A composition according to claim 17, wherein said at least one cationic surfactant is chosen from behenyltrimethylammonium salts, stearamidopropyidimethyl(myristyl acetate)ammonium salts, Quatemium-27 and Quaternium-83.

41. A composition according to claim 17, wherein the at least one cationic surfactant is present in an amount ranging from 0.1% to 10% by weight relative to the total weight of the composition.

42. A composition according to claim 41, wherein the at least one cationic surfactant is present in an amount ranging from 0.5% to 7% by weight relative to the total weight of the composition.

43. A composition according to claim 42, wherein the at least one cationic surfactant is present in an amount ranging from 1% to 5% by weight relative to the total weight of the composition.

44. A composition according to claim 1 further comprising at least one surfactant chosen from anionic, nonionic, and amphoteric surfactants.

45. A composition according to claim 44, wherein the at least one surfactant chosen from anionic, nonionic, and amphoteric surfactants is present in an amount ranging from 0.1% to 60% by weight, relative to the total weight of the composition.

46. A composition according to claim 45, wherein the at least one surfactant chosen from anionic, nonionic, and amphoteric surfactants is present in an amount ranging from 3% to 40% by weight, relative to the total weight of the composition.

47. A composition according to claim 46, wherein the at least one surfactant chosen from anionic, nonionic, and amphoteric surfactants is present in an amount ranging from 5% to 30% by weight, relative to the total weight of the composition.

48. A composition according to claim 44, wherein the at least one surfactant chosen from anionic, nonionic, and amphoteric surfactants comprises at least one anionic surfactant salt chosen from alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates.

49. A composition according to claim 44, wherein said at least one surfactant is chosen from anionic surfactants chosen from alkaline salts, sodium salts, ammonium salts, amine salts, amino alcohol salts and magnesium salts.

50. A composition according to claim 48, wherein said alkyl and acyl portions of radicals of said salts comprise 1 and from 8 to 24 carbon atoms, and said aryl portions of radicals of said salts are phenyl.

51. A composition according to claim 44, wherein said at least one surfactant is chosen from anionic surfactants chosen from fatty acid salts, acyl lactates wherein the acyl radical comprises 8 to 20 carbon atoms, and weakly anionic surfactants.

52. A composition according to claim 51, wherein said fatty acid salts are chosen from the salts of oleic acid, ricinoleic acid, palmitic acid, stearic acid, coconut oil acid and hydrogenated coconut oil acid.

53. A composition according to claim 44, wherein said at least one surfactant is chosen from anionic surfactants chosen from alkyl-D-galactosiduronic acids and their salts, polyoxyalkylenated ($C_6$–$C_{24}$) alkyl ether carboxylic acids and their salts, polyoxyalkylenated ($C_6$–$C_{24}$) alkylaryl ether carboxylic acids and their salts, and polyoxyalkylenated ($C_6$–$C_{24}$) alkylamido ether carboxylic acids and their salts.

54. A composition according to claim 51, wherein said weakly anionic surfactants comprise from 2 to 50 ethylene oxide groups.

55. A composition according to claim 48, wherein said at least one anionic surfactant salt is chosen from alkyl sulfates and alkyl ether sulfates.

56. A composition according to claim 44, wherein said at least one surfactant is chosen from nonionic surfactants chosen from polyethoxylated, polypropoxylated and polyglycerolated fatty acids, alkylphenols, α-diols and alcohols having a fatty aliphatic chain comprising 8 to 18 carbon atoms, wherein the number of ethylene oxide and propylene oxide groups ranges from 2 to 50 and the number of glycerol groups ranges from 2 to 30, copolymers of ethylene oxide and of propylene oxide, condensates of ethylene oxide and of propylene oxide with fatty alcohols, polyethoxylated fatty amides comprising from 2 to 30 mol of ethylene oxide, polyglycerolated fatty amides comprising on average 1 to 5 glycerol groups, polyethoxylated fatty amines comprising from 2 to 30 mol of ethylene oxide, oxyethylenated fatty acid esters of sorbitan comprising from 2 to 30 mol of ethylene oxide, fatty acid esters of sucrose, fatty acid esters of polyethylene glycol, alkylpolyglycosides, N-alkylglucamine derivatives, and amine oxides.

57. A composition according to claim 56, wherein said polyglycerolated fatty amides comprise on average 1.5 to 4 glycerol groups.

58. A composition according to claim 56, wherein said amine oxides are chosen from ($C_{10}$–$C_4$)alkylamine oxides and N-acylaminopropylmorpholine oxides.

59. A composition according to claim 56, wherein said nonionic surfactants are chosen from alkylpolyglycosides.

60. A composition according to claim 44, wherein said at least one surfactant is chosen from amphoteric surfactants chosen from aliphatic secondary and tertiary amine derivatives wherein the aliphatic radical is chosen from linear and branched chain radicals comprising 8 to 22 carbon atoms and comprising at least one water-soluble anionic group, ($C_8$–$C_{20}$)alkylbetaines, sulfobetaines, ($C_8$–$C_{20}$)alkylamido ($C_1$–$C_6$)alkylbetaines, and ($C_8$–$C_{20}$)alkylamido($C_1$–$C_6$)alkylsulfobetaines.

61. A composition according to claim 60, wherein said at least one water-soluble anionic group is chosen from carboxylates, sulfonates, sulfates, phosphates and phosphonates.

62. A composition according to claim 60, wherein said amine derivatives are chosen from the compounds:

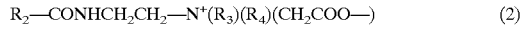

$$R_2\text{—CONHCH}_2\text{CH}_2\text{—N}^+(R_3)(R_4)(CH_2COO\text{—}) \qquad (2)$$

in which:
$R_2$ is chosen from alkyl radicals derived from an acid $R_2$—COOH present in hydrolysed coconut oil, heptyl, nonyl and undecyl radicals,
$R_3$ is chosen from β-hydroxyethyl groups, and
$R_4$ is chosen from carboxymethyl groups; and

$$R_5\text{—CONHCH}_2\text{CH}_2\text{—N(B)(C)} \qquad (3)$$

in which:
(B) is —CH$_2$CH$_2$OX', with X' chosen from a —CH$_2$CH$_2$—COOH group and a hydrogen atom,
(C) is —(CH$_2$)$_z$—Y', with z=1 or 2, and with Y' chosen from —COOH and —CH$_2$—CHOH—SO$_3$H radicals,
$R_5$ is chosen from alkyl radicals and unsaturated $C_{17}$ radicals.

63. A composition according to claim 62, wherein said alkyl radicals $R_5$ are chosen from (a) alkyl radicals of an acid $R_5$—COOH present in oils chosen from coconut oil and hydrolysed linseed oil, and (b) $C_{17}$ alkyl radicals and the iso forms.

64. A composition according to claim 62, wherein said alkyl radicals of said $R_5$ are chosen from alkyl radicals chosen from $C_7$, $C_9$, $C_{11}$, and $C_{13}$ alkyl radicals.

65. A composition according to claim 44, wherein said at least one surfactant is chosen from at least two surfactants of different types.

66. A composition according to claim 65, wherein said at least two surfactants of different types are chosen from (a) more than one anionic surfactant, (b) at least one anionic surfactant and at least one amphoteric surfactant, and (c) at least one anionic surfactant and and at least one nonionic surfactant.

67. A composition according to claim 44, wherein said at least one surfactant is chosen from anionic surfactants chosen from ($C_{12}$–$C_{14}$)alkyl sulfates of sodium, of triethanolamine and of ammonium, ($C_{12}$–$C_{14}$)alkyl ether sulfates of sodium, of triethanolamine and of ammonium, oxyethylenated with 2.2 mol of ethylene oxide, sodium cocoyl isethionate, and sodium ($C_{14}$–$C_{16}$)-α-olefin sulfonate, and from an amphoteric surfactant chosen from either:

amine derivatives comprising disodium cocoamphodipropionate and sodium cocoamphopropionate, or amphoteric surfactants of zwitterionic type.

68. A composition according to claim 67, wherein said amphoteric surfactants of zwitterionic type are chosen from alkylbetaines.

69. A composition according to claim 68, wherein said alkylbetaines are chosen from cocobetaine.

70. A composition according to claim 1 further comprising at least one additive chosen from fragrances, nacreous agents, preserving agents, silicone sunscreens, non-silicone sunscreens, vitamins, provitamins, amphoteric, anionic and nonionic polymers, proteins, protein hydrolysates, 18-methyleicosanoic acid, hydroxy acids, panthenol, volatile and non-volatile, cyclic and linear and crosslinked, modified and non-modified silicones, ceramides, pseudoceramides, plant, animal, mineral and synthetic oils, and any other additive conventionally used in cosmetics which does not substantially adversely affect the properties of the compositions according to the invention.

71. A composition according to claim 70, wherein said at least one additive is present in an amount ranging from 0 to 20% by weight relative to the total weight of the composition.

72. A rinse-out conditioner, a leave-in conditioner, a composition for permanent-waving the hair, a composition for straightening the hair, a composition for dyeing the hair, a composition for bleaching the hair, a rinse-out composition to be applied before a procedure chosen from dyeing, bleaching, permanent-waving and straightening the hair, a rinse-out composition to be applied after a procedure chosen from dyeing, bleaching, permanent-waving and straightening the hair, a rinse-out composition to be applied between the two steps of a permanent-waving operation, a rinse-out composition to be applied between the two steps of a hair-straightening operation, a washing composition for the body, an aqueous lotion, an aqueous-alcoholic lotion, a gel, a milk, a cream, an emulsion, a thickened lotion, a mousse, or a detergent composition comprising a washing base comprising, in a cosmetically acceptable medium, (1) at least one silicone copolymer with a dynamic viscosity ranging from $1\times10^6$ to $100\times10^6$ cP, resulting from the addition reaction, in the presence of a catalyst, of at least:

(a) one polysiloxane of formula (I):

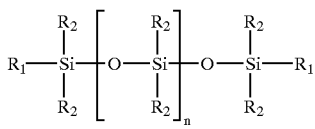

(I)

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1\times10^6$ mm$^2$/s; and (b) at least one silicone compound comprising at least one and not more than two groups capable of reacting with the groups $R_1$ of the polysiloxane (a), wherein:

at least one of the compounds of type (a) and (b) comprises an aliphatic group comprising an ethylenic unsaturation, and (2) at least one cationic polymer.

73. An aqueous or aqueous-alcoholic lotion according to claim 72, said lotion being suitable for skin care or for hair care.

74. A gel, a milk, a cream, an emulsion, a thickened lotion or a mousse according to claim 72, wherein said gel, milk, cream, emulsion, thickened lotion or mousse is suitable to be applied to at least one keratin material chosen from skin, nails, eyelashes, lips and hair.

75. A detergent composition comprising a washing base according to claim 72, wherein said composition is chosen from shampoos, shower gels, bubble baths and make-up-removing products.

76. A detergent composition comprising a washing base according to claim 72, wherein said washing base comprises at least one surfactant chosen from anionic, amphoteric, nonionic and cationic surfactants.

77. A detergent composition according to claim 76, wherein said at least one surfactant is present in an amount effective to provide satisfactory foaming power and satisfactory detergent power.

78. A detergent composition comprising a washing base according to claim 76, wherein said washing base is present in an amount ranging from 4% to 50% by weight, relative to the total weight of the final composition.

79. A detergent composition comprising a washing base according to claim 78, wherein said washing base is present in an amount ranging from 6% to 35% by weight, relative to the total weight of the final composition.

80. A detergent composition comprising a washing base according to claim 79, wherein said washing base is present in an amount ranging from 8% to 25% by weight, relative to the total weight of the final composition.

81. A process of washing or caring for a keratin material comprising applying to said keratin material a composition comprising, in a cosmetically acceptable medium, (1) at least one silicone copolymer with a dynamic viscosity ranging from $1\times10^6$ to $100\times10^6$ cP, resulting from the addition reaction, in the presence of a catalyst, of at least:

(a) one polysiloxane of formula (I):

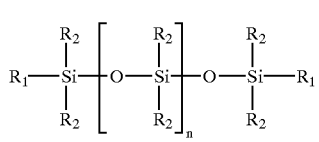

(I)

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups $R_1$ of the polysiloxane (a), wherein:
at least one of the compounds of type (a) and (b) comprises an aliphatic group comprising an ethylenic unsaturation, and (2) at least one cationic polymer.

82. A process for treating a keratin material comprising applying to said keratin material a composition comprising, in a cosmetically acceptable medium, (1) at least one silicone copolymer with a dynamic viscosity ranging from $1 \times 10^6$ to $100 \times 10^6$ cP, resulting from the addition reaction, in the presence of a catalyst, of at least:

(a) one polysiloxane of formula (I):

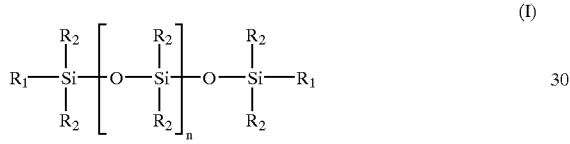

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups $R^1$ of the polysiloxane (a), wherein:
at least one of the compounds of type (a) and (b) comprises an aliphatic group comprising an ethylenic unsaturation, and (2) at least one cationic polymer, and optionally rinsing said composition out with water.

83. A process for washing or treating a keratin material according to claim 82, wherein said keratin material is chosen from hair, skin, eyelashes, eyebrows, nails, lips and scalp.

84. A process for manufacturing a cosmetic product comprising including in said product (1) at least one silicone copolymer with a dynamic viscosity ranging from $1 \times 10^6$ to $100 \times 10^6$ cP, resulting from the addition reaction, in the presence of a catalyst, of at least:

(a) one polysiloxane of formula (I):

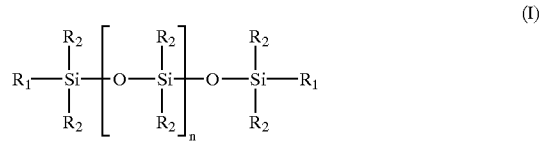

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, and can optionally further comprise functional groups, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups $R_1$ of the polysiloxane (a), wherein:
at least one of the compounds of type (a) and (b) comprises an aliphatic group comprising an ethylenic unsaturation, and (2) at least one cationic polymer.

85. A composition according to claim 1, wherein said cationic polymer is chosen from:

(1) homo- and co-polymers derived from at least one monomer chosen from acrylic esters, methacrylic esters and amides, wherein said homo- and co-polymers comprise at least one unit chosen from units of formulae:

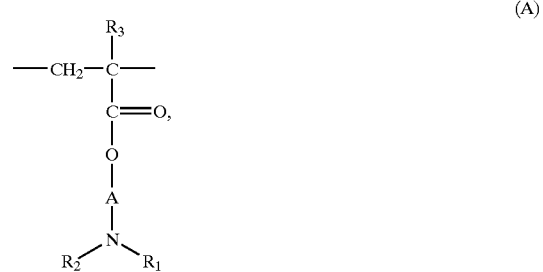

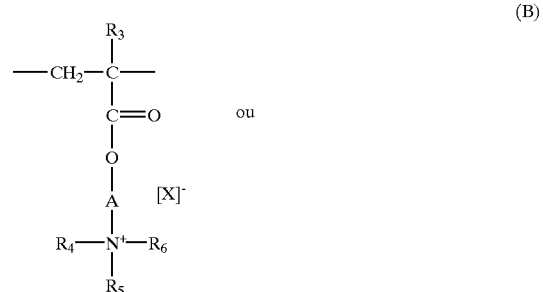

-continued

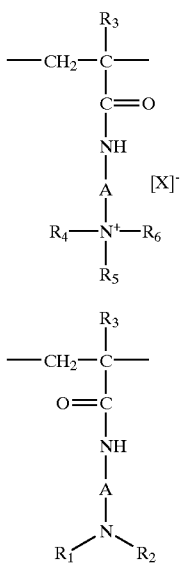

wherein:
  $R_3$, which may be identical or different, are each chosen from hydrogen atoms and $CH_3$ groups;
  A, which may be identical or different, are each chosen from linear and branched alkyl groups comprising from 1 to 6 carbon atoms and hydroxyalkyl groups comprising from 1 to 4 carbon atoms;
  $R_4$, $R_5$ and $R_6$, which may be identical or different, are each chosen from alkyl groups comprising from 1 to 18 carbon atoms and benzyl groups;
  $R_1$ and $R_2$, which may be identical or different, are each chosen from hydrogen atoms and alkyl groups comprising from 1 to 6 carbon atoms;
  $X^-$ is an anion chosen from anions derived from at least one inorganic acid and anions derived from at least one organic acid;
(2) cellulose ether derivatives comprising quaternary ammonium groups;
(3) cationic cellulose derivatives;
(4) cationic polysaccharides;
(5) polymers comprising (i) at least one piperazinyl unit and (ii) at least one group chosen from divalent alkylene groups and divalent hydroxyalkylene groups, wherein said at least one group optionally comprises at least one chain chosen from straight chains and branched chains, wherein said at least one chain is optionally interrupted by at least one entity chosen from oxygen atoms, sulphur atoms, nitrogen atoms, aromatic rings and heterocyclic rings,
  the oxidation products of said polymers and the quaternization products of said polymers;
(6) water-soluble polyamino amides which may be prepared via at least one polycondensation reaction of at least one acidic compound and at least one polyamine compound, wherein said polyamino amides may be crosslinked with at least one crosslinking agent chosen from epihalohydrins, diepoxides, dianhydrides, unsaturated dianhydrides, bis-unsaturated derivatives, bis-halohydrins, bis-azetidiniums, bis-haloacyidiamines, bis-alkyl halides and oligomers derived from reaction of at least one difunctional compound with at least one compound chosen from bis-halohydrins, bis-azetidiniums, bis-haloacyldiamines, bis-alkyl halides, epihalohydrins, diepoxides and bis-unsaturated derivatives, wherein said crosslinking agent may be used in a proportion generally ranging from 0.025 mol to 0.35 mol per amine group of said polyamino amide, wherein said polyamino amides may optionally be alkylated, and wherein if said polyamino amides comprise at least one tertiary amine group, said polyamino amides may optionally be quaternized;
(7) polyamino amide derivatives derived from condensation of at least one polyalkylene polyamine with at least one polycarboxylic acid, followed by alkylation with at least one difunctional agent;
(8) polymers derived from reaction of (i) at least one polyalkylene polyamine comprising two primary amine groups and at least one secondary amine group with (ii) at least one dicarboxylic acid chosen from diglycolic acid and saturated aliphatic dicarboxylic acids comprising from 3 to 8 carbon atoms;
(9) cyclopolymers of alkyldiallylamine and cyclopolymers of dialkyldiallylammonium;
(10) quaternary diammonium polymers comprising at least two repeating units of formula:

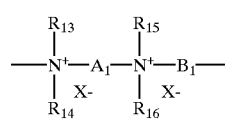

(VII)

wherein:
  $R_{13}$, $R_{14}$, $R_{15}$ and $R_{16}$, which may be identical or different, are each chosen from aliphatic groups comprising from 1 to 20 carbon atoms, alicyclic groups comprising from 1 to 20 carbon atoms, arylaliphatic groups comprising from 1 to 20 carbon atoms, lower hydroxyalkylaliphatic groups, or
  at least two of said $R_{13}$, $R_{14}$, $R_{15}$ and $R_{16}$, together with the nitrogen atoms to which they are attached, form at least one heterocycle optionally comprising an additional heteroatom other than nitrogen, or
  $R_{13}$, $R_{14}$, $R_{15}$ and $R_{16}$, which may be identical or different, are each chosen from linear and branched $C_1$–$C_6$ alkyl groups substituted with at least one group chosen from nitrile groups, ester groups, acyl groups, amide groups and groups chosen from groups of formulae —CO—O—$R_7$—D and —CO—NH—$R_{17}$—D wherein $R_{17}$ is chosen from alkylene groups and D is chosen from quaternary ammonium groups;
  $A_1$ and $B_1$, which may be identical or different, are each chosen from polymethylene groups comprising from 2 to 20 carbon atoms, chosen from linear and branched, saturated and unsaturated polymethylene groups wherein said polymethylene groups may optionally comprise, optionally linked to and optionally intercalated in the main chain, at least one entity chosen from aromatic rings, oxygen atoms, sulphur atoms, sulphoxide groups, sulphone groups, disulphide groups, amino groups, alkylamino groups, hydroxyl groups, quaternary ammonium groups, ureido groups, amide groups and ester groups; and
  $X^-$ is an anion chosen from anions derived from inorganic acids and anions derived from organic acids; and
  $A_1$, $R_{13}$ and $R_{15}$ may optionally form, together with the two nitrogen atoms to which they are attached, at least one piperazine ring;

with the proviso that if $A_1$ is chosen from linear and branched, saturated and unsaturated alkylene groups and linear and branched, saturated and unsaturated hydroxyalkylene groups, $B_1$ may also be chosen from groups of formula:

$$(CH_2)_n-CO-D-OC-(CH_2)_n-$$

wherein D is chosen from:
a) glycol residues of formula: $-O-Z-O-$, wherein Z is chosen from linear and branched hydrocarbon groups and groups chosen from groups of formulae:

$$-(CH_2-CH_2-O)_x-CH_2-CH_2-$$

and $$-[CH_2-CH(CH_3)-O]_y-CH_2-CH(CH_3)-$$

wherein x and y, which may be identical or different, are each chosen from integers ranging from 1 to 4 (in which case x and y represent a defined and unique degree of polymerization) and any number ranging from 1 to 4 (in which case x and y represent an average degree of polymerization);
b) bis-secondary diamine residues such as piperazine derivatives;
c) bis-primary diamine residues chosen from residues of formula: $-NH-Y-NH-$, wherein Y is chosen from linear and branched hydrocarbon groups and residues of formula $-CH_2-CH_2-S-S-CH_2-CH_2-$; and
d) ureylene groups of formula: $-NH-CO-NH-$;

(11) polyquaternary ammonium polymers comprising at least one unit of formula (VIII):

$$-\underset{\underset{R_{19}}{|}}{\overset{\overset{R_{18}}{|}}{N^+}}-(CH_2)_r-NH-CO-(CH_2)_q-CO-NH-(CH_2)_s-\underset{\underset{X^- \ R_{21}}{|}}{\overset{\overset{R_{20}}{|}}{N^+}}-A- \quad (VIII)$$

$$X^-$$

wherein:
$R_{18}$, $R_{19}$, $R_{20}$ and $R_{21}$, which may be identical or different, are each chosen from hydrogen atoms, methyl groups, ethyl groups, propyl groups, β-hydroxyethyl groups, β-hydroxypropyl groups and $-CH_2CH_2(OCH_2CH_2)_pOH$ groups wherein p is an integer ranging from 0 to 6, with the proviso that $R_{18}$, $R_{19}$, $R_{20}$ and $R_{21}$ are all not simultaneously chosen from hydrogen atoms;
r and s, which may be identical or different, are each chosen from integers ranging from 1 to 6;
q is an integer ranging from 1 to 34;
$X^-$ is an anion, such as a halide,
A is chosen from dihalide groups and groups of formula $-CH_2-CH_2-O-CH_2-CH_2-$;

(12) quaternary polymers of vinylpyrrolidone and quaternary polymers of vinylimidazole;

(13) polyamines referred to as "Polyethylene glycol (15) Tallow Polyamine" in the CTFA dictionary;

(14) crosslinked polymers of methacryloyloxy($C_1$–$C_4$)alkyltri($C_1$–$C_4$)alkylammonium salts; and

(15) polyalkyleneimines, polymers comprising at least one vinylpyridine unit, polymers comprising at least one vinylpyridinium unit, condensates of polyamines, condensates of epichlorohydrin, quaternary polyureylenes and chitin derivatives.

86. A composition according to claim 85, wherein said cationic cellulose derivatives are chosen from cellulose copolymers grafted with at least one water-soluble quaternary ammonium monomer and cellulose derivatives grafted with at least one water-soluble quaternary ammonium monomer.

87. A composition according to claim 85, wherein said $X^-$ of formula (Vll) is chosen from chloride atoms and bromine atoms.

88. A composition according to claim 85, wherein said polyalkyleneimines are chosen from polyethyleneimines.

89. A composition according to claim 1, wherein said at least one cationic polymer is chosen from quaternary cellulose ether derivatives, cyclopolymers, cationic polysaccharides, vinylpyrrolidone/methacrylamidopropyldimethylamine copolymers and crosslinked homo- and copolymers of methacryloyloxy ($C_1$–$C_4$)alkyltri($C_1$–$C_4$)alkylammonium salts.

90. A composition according to claim 1, wherein said at least one cationic polymer is present in an amount ranging from 0.001% to 20% by weight relative to the total weight of said composition.

91. A composition according to claim 90, wherein said at least one cationic polymer is present in an amount ranging from 0.01% to 10% by weight relative to the total weight of said composition.

* * * * *

UNITED STATES PATENT AND TRADEMARK OFFICE
CERTIFICATE OF CORRECTION

PATENT NO.    : 6,451,298 B1
DATED         : September 17, 2002
INVENTOR(S)   : Sandrine Decoster et al.

It is certified that error appears in the above-identified patent and that said Letters Patent is hereby corrected as shown below:

Column 21,
Line 18, "to30" should read -- to 30 --.

Column 22,
Line 11, after "$R_{16}$" delete the comma.

Column 23,
Line 5, "to4" should read -- to 4 --.
Line 52, "diacyloxyethyidimethylammonium" should read
-- diacyloxyethyldimethylammonium --.
Line 54, "monoacyloxyethyidihydroxyethylmethylammonium" should read
-- monoacyloxyethyldihyroxyethylmethylammonium --.

Column 24,
Line 57, "stearamidopropyidimethyl" should read -- stearamidopropyldimethyl --.
Line 58, "Quatemium-27" should read -- Quaternium-27 --.

Column 26,
Line 19, "($C_{10}$-$C_4$)alkylamine" should read -- ($C_{10}$-$C_{14}$)alkylamine --.

Column 27,
Line 5, delete the second occurrence of "and".

Column 29,
Line 6, after "to" insert a space.
Line 49, "$R^1$" should read -- $R_1$ --.

Column 30,
Line 60, "ou" should read -- or --.

Column 31,
Line 37, "to6" should read -- to 6 --.
Line 64, "bis-haloacyidiames" should read -- bis-haloacyldiamines --.

UNITED STATES PATENT AND TRADEMARK OFFICE
CERTIFICATE OF CORRECTION

PATENT NO.    : 6,451,298 B1
DATED         : September 17, 2002
INVENTOR(S)   : Sandrine Decoster et al.

It is certified that error appears in the above-identified patent and that said Letters Patent is hereby corrected as shown below:

<u>Column 32,</u>
Line 46, "$R_7$" should read -- $R_{17}$ --.

<u>Column 33,</u>
Line 14, after the formula, insert a semicolon.

Signed and Sealed this

Eighteenth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,451,298 B1
DATED : September 17, 2002
INVENTOR(S) : Sandrine Decoster et al.

It is certified that error appears in the above-identified patent and that said Letters Patent is hereby corrected as shown below:

Column 21,
Line 18, "to30" should read -- to 30 --.

Column 22,
Line 11, after "$R_{16}$" delete the comma.

Column 23,
Line 5, "to4" should read -- to 4 --.
Line 52, "diacyloxyethyidimethylammonium" should read
-- diacyloxyethyldimethylammonium --.
Line 54, "monoacyloxyethyidihydroxyethylmethylammonium" should read
-- monoacyloxyethyldihydroxyethylmethylammonium --.

Column 24,
Line 57, "stearamidopropyidimethyl" should read -- stearamidopropyldimethyl --.
Line 58, "Quatemium-27" should read -- Quaternium-27 --.

Column 26,
Line 19, "($C_{10}$-$C_4$)alkylamine" should read -- ($C_{10}$-$C_{14}$)alkylamine --.

Column 27,
Line 5, delete the second occurrence of "and".

Column 29,
Line 6, after "to" insert a space.
Line 49, "$R^1$" should read -- $R_1$ --.

Column 30,
Line 60, "ou" should read -- or --.

Column 31,
Line 37, "to6" should read -- to 6 --.
Line 64, "bis-haloacyidiames" should read -- bis-haloacyldiamines --.

UNITED STATES PATENT AND TRADEMARK OFFICE
CERTIFICATE OF CORRECTION

PATENT NO. : 6,451,298 B1
DATED : September 17, 2002
INVENTOR(S) : Sandrine Decoster et al.

It is certified that error appears in the above-identified patent and that said Letters Patent is hereby corrected as shown below:

<u>Column 32,</u>
Line 46, "$R_7$" should read -- $R_{17}$ --.

<u>Column 33,</u>
Line 14, after the formula, insert a semicolon.

This certificate supersedes Certificate of Correction issued February 18, 2003.

Signed and Sealed this

Third Day of January, 2006

JON W. DUDAS
*Director of the United States Patent and Trademark Office*